United States Patent [19]

Langone

[11] 4,430,318
[45] Feb. 7, 1984

[54] IMMUNOASSAY UTILIZING $^{125}$I PROTEIN A

[75] Inventor: John J. Langone, Germantown, Md.

[73] Assignee: The United States of America as represented by the Department of Health and Human Services, Washington, D.C.

[21] Appl. No.: 307,536

[22] Filed: Oct. 1, 1981

Related U.S. Application Data

[63] Continuation of Ser. No. 964,654, Nov. 29, 1978.

[51] Int. Cl.$^3$ .................. G01N 33/48; G01N 33/60
[52] U.S. Cl. ..................................... 424/1.1; 260/112 R; 435/883; 436/501; 436/518; 436/520; 436/539; 436/542; 436/828; 436/804
[58] Field of Search ................... 424/1, 1.5; 23/230 B

[56] References Cited

U.S. PATENT DOCUMENTS

| | | | |
|---|---|---|---|
| 3,850,798 | 11/1974 | Sjöquist | 210/31 C |
| 3,966,898 | 6/1976 | Sjöquist et al. | 424/12 |
| 4,230,685 | 10/1980 | Senyei et al. | 424/12 |

OTHER PUBLICATIONS

Langone, John J., Methods in Enzymology, vol. 70, pp. 356-375, Academic Press (1980).
Bolton, A. E. and Hunter, W. M., Biochemical Journal, vol. 133, p. 529 (1973).
Langone, John J. et al., Journal of Immunological Methods, vol. 18, pp. 281-293 (1978), vol. 24, pp. 269-285 (1978).
Dorval, G. et al., J. Immunological Methods, vol. 7, p. 237 (1975).
Meltzer, P. M. et al., Journal of Immunological Methods, vol. 17, p. 163 (1977).
Bikerfeld, P. et al., Journal of Immunological Methods, vol. 6, p. 249 (1975).
Hunter, W. M. et al., Nature (London) vol. 194, p. 495 (1962).

Primary Examiner—Christine M. Nucker
Assistant Examiner—M. Moskowitz
Attorney, Agent, or Firm—John S. Roberts, Jr.

[57] ABSTRACT

An improved method for the preparation of $^{125}$I-labelled Protein A ($^{125}$I PA) of high specific and functional activity. $^{125}$I PA has been used in combination with purified rabbit IgG (immunoglobulin G) bound to a solid support to develop a competitive binding assay capable of detecting Protein A or human, rabbit and guinea pig IgG at the nanogram level. Additionally, $^{125}$I PA may be used to detect methotrexate, leucovorin and similar substances.

$^{125}$I PA has also been used to detect IgG anti-Forssman antibody bound to sheep erythrocytes and to line-1 and line-10 tumor cells and as an indirect assay for tumor associated antigen in the ascitic fluid of tumor-bearing guinea pigs.

Additionally, an improved method of preparation of iodination of Protein A is utilized. This procedure used the Bolton-Hunter (1973) reagent of radioactive iodine in benzene which carrier is evaporated. The PA is added or attached while in an amino acid mixture and separation is per column utilizing Sephadex G-25 and VBS-gel.

8 Claims, 1 Drawing Figure

IMMUNOASSAY UTILIZING $^{125}$I PROTEIN A

This is a continuation, of application Ser. No. 964,654, filed Nov. 29, 1978.

This invention relates to an improved method for the preparation of $^{125}$I-labelled Protein A ($^{125}$I PA) of high specific and functional activity. $^{125}$I PA has been used in combination with purified rabbit IgG (immunoglobulin G) bound to a solid support to develop a competitive binding assay capable of detecting Protein A or human, rabbit and guinea pig IgG at the nanogram level. Additionally, $^{125}$I PA may be used to detect methotrexate, leucovorin and similar substances.

$^{125}$I PA has also been used to detect IgG anti-Forssman antibody bound to sheep erythrocytes and to line-1 and line-10 tumor cells and as an indirect assay for tumor associated antigen in the ascitic fluid of tumor-bearing guinea pigs.

Additionally, an improved method of preparation of iodination of Protein A is utilized. This procedure used the Bolton-Hunter (1973) reagent of radioactive iodine in benzene which carrier is evaporated. The PA is added or attached while in an amino acid mixture and separation is per column utilized Sephadex G-25 and VBS-gel.

PROTEIN A

Protein A is a protein isolated from the cell wall of *Staphylococcus aureus* and is described in a professional pamphlet of Pharmacia Fine Chemicals, Inc., Piscataway, N.J. It is antigenic in nature and characteristically has an unusual property of interacting with and forming precipitates with a wide variety of IgG molecules from several species.

Protein A, isolated from *Staphylococcus aureus*, has been shown to bind specifically to the Fc fragment of IgG subclasses 1, 2 and 4 of most species tested. This selectivity has been the basis of immunoassays for the detection of antibody (and indirectly of antigen) on the surfaces of cells. In addition, Protein A-containing *S. aureus* has been used in a solid phase assay for alphafetoprotein ($\alpha$-FP) present in human serum using $^{125}$I $\alpha$-FP and anti-$\alpha$-FP.

I LABELLED PROTEIN A PREPARATION

The general iodination procedure of Bolton and Hunter (1973) was used. A solution of 0.2 mCi of Bolton-Hunter reagent (Amersham/Searle, Arlington Heights, IL, specific activity >1400 Ci/mmole) in 150 $\mu$l of benzene was evaporated under a gentle stream of air. Protein A (50 $\mu$g, added in 0.1 ml of a 5.0 mg/ml solution in 0.05 M phosphate, pH 8.0) was added to the residue and allowed to stand at 20° C. for 15 minutes. An amino acid mixture (0.1 ml) was added to react with excess Bolton-Hunter reagent. After 30 minutes at 20° C., 0.5 ml of BVS-gel was added and the reaction mixture chromatographed on a column (16×1.5 cm) of Sephadex G-25 (Pharmacia) wet-packed and eluted with VBS-gel; 1.3 ml fractions were collected.

PRIOR ART STATEMENT

U.S. Pat. No. 3,966,898-An early patented disclosure, as in Examples 3 and 4 measuring antibody bound to the antigen IgE (3) and the detection of IgE on the beads (4). This patent lacks quantitative measurement of either fluid phase antibody or antigen.

Langone et al, *Journal of Immunological Methods*, 18: 281-293 (1977).

Langone et al, *The Journal of Immunology*, 121(1): 327-332 (July 1978).

Langone et al, *The Journal of Immunology*, 121(1): 333-338 (July 1978).

Langone et al, "Immunoassay of Leucovorin: Use of $^{125}$I Protein A to Detect Immunological Binding," [submitted to *Analytical Biochemistry*].

Langone et al, "A Solid Phase Immunoassay for Human Immunoglobulin E: Use of $^{125}$I Protein A as the Tracer," [accepted for publication in *Analytical Biochemistry*].

IMMUNOASSAY METHODS AND SYSTEMS

In the general immunoassay procedure to determine fluid phase Protein A or IgG, 0.1 ml of test sample or buffer and 0.1 ml of $^{125}$I PA (approximately 25,000 cpm) were incubated at 30° C. for 30 minutes. A 50-$\mu$l sample of standard Immunobead suspension was added and the mixture incubated at 30° C. for 60 minutes. Three millimeters of cold VBS-gel was added and the tubes centrifuged at 1,000 g for 5 minutes at 4° C. After two more washes, the radioactivity in the bead pellets was determined by counting in a Packard model 5360 auto gamma spectrometer. Under these asssay conditions, which were determined to be optimal, control (maximum) binding of $^{125}$I PA to the Immunobeads was about 7,500 cpm. The degree of inhibition of binding was calculated by determining the percentage of cpm displaced from the $^{125}$I PA Immunobead complex by known amounts of unlabelled inhibitors. The amounts of IgG in a test sample was calculated by comparing the observed percent inhibition with the standard inhibition curve.

BINDING OF $^{125}$I PA TO IMMOBILIZED IgG

This invention has developed a protein binding assay for IgG based on the competition between fluid phase IgG in a test sample and rabbit IgG covalently bound to a solid support (Immunobeads) for a limited amount of $^{125}$I PA. The assay is fast, simple to perform and the results are highly reproducible. The curve in FIG. 1a shows the amount of radiolabel bound to the Immunobeads as a function of bead concentration. Different amounts of standard bead suspension (50 mg of beads suspended in 20 ml of VBS-gel) were incubated at 30° C. for 60 minutes with approximately 25,000 cpm of labelled Protein A in a total volume of 0.30 ml VBS-gel. The resin was washed three times with buffer (experiments had shown that two washes were sufficient and that no loss of radioactivity from the beads occurred after the second wash) and the radioactivity in the pellets counted. The same results were obtained if the beads were centrifuged after washing or were collected by filtration on polycarbonate filters (FIG. 1a). At the highest bead concentration tested, approximately 70% of the added radioactivity was bound. Based on these results, 50 $\mu$l of the standard bead suspension (equivalent to 0.4 $\mu$g IgG) would bind about 7500 cpm (30% of added radioactivity). The amount of label bound to the beads has been corrected for a background of less than 150 cpm which adhered to control tubes in the absence of beads or onto the filter.

DETERMINATION OF FLUID PHASE IgG

Figure 1A:
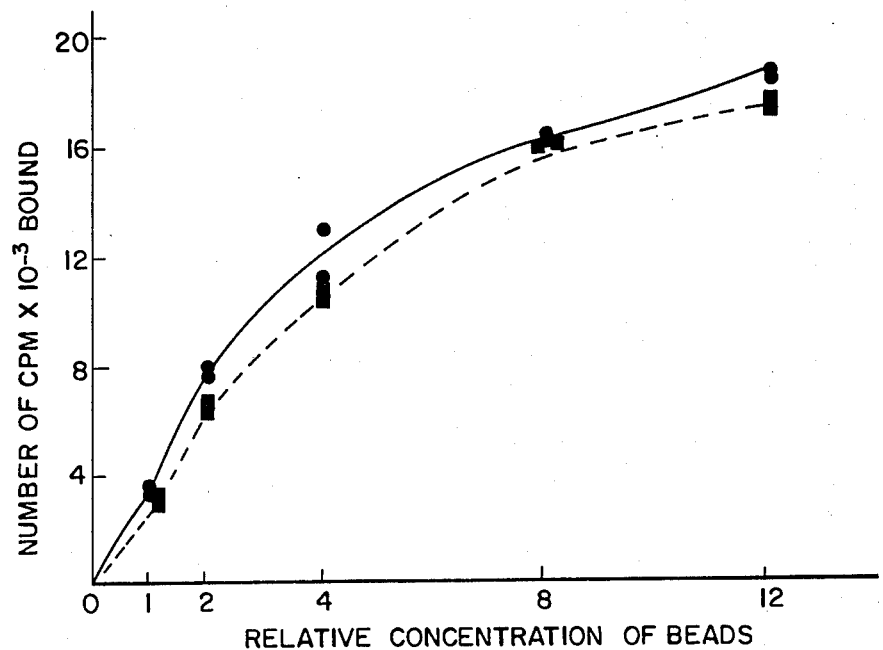
FIG. 1 is a diagrammatic graph (a) and (b) which shows in (a) the binding of $^{125}$I PA to IgG Immunobeads as a function of bead concentration. A constant amount (0.1 ml, 24,000 cpm) of radiolabel was added to the beads, incubated at 30° C. for 60 minutes before the beads were washed and collected by centrifugation (●————●) or by filtration using polycarbonate filters (●————●). A relative concentration of I=25 μl of bead suspension. In (b) is shown the kinetics of binding $^{125}$I PA (27,000 cpm added) to a constant amount of IgG Immunobeads at 30° C.
Figure 1B:
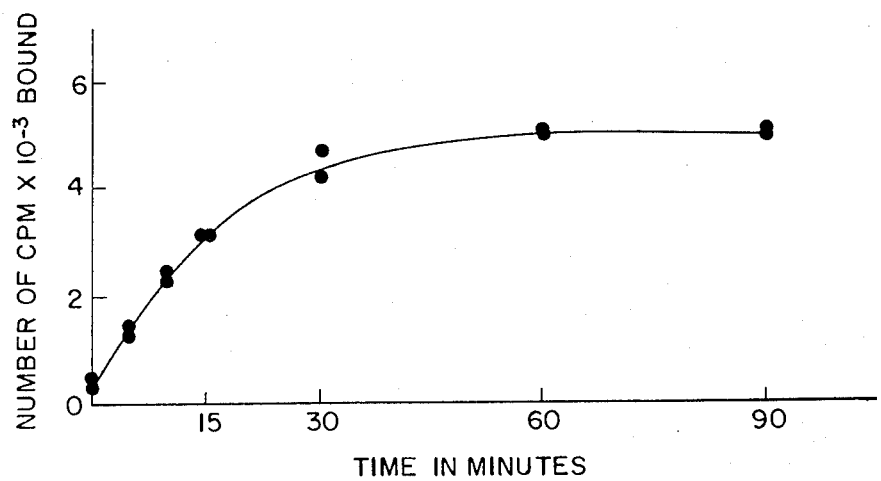

An immunoassay was utilized to determine the levels of IgG in normal human, rabbit and strain-2 guinea pig serum. Dilutions of serum were tested for their ability to inhibit the binding of $^{125}$I PA to the Immunobeads. Based on the inhibition observed for known amounts of standard samples of IgG, the concentration of IgG in the test samples can be calculated. The data in Table 1 below demonstrate that the levels among the sera from each species vary only slightly and agree well with available reported values. The average level of IgG in the three sets of sera was 9.5, 4.6 and 13.6 mg/ml for human, strain 2 guinea pig and rabbit, respectively.

TABLE 1

Concentration of IgG in Normal Sera (mg/ml ± SE)*

| Sample No. | Species | | |
|---|---|---|---|
| | Human | Rabbit | Strain-2 Guinea Pig |
| 1 | 10.0 ± 0.5 | 14.5 ± 0.5 | 3.3 ± 0.3 |
| 2 | 10.0 ± 0.0 | 14.5 ± 0.5 | 2.0 ± 0.1 |
| 3 | 11.3 ± 0.7 | 13.5 ± 0.5 | 5.9 ± 0.1 |
| 4 | 9.0 ± 0.5 | 12.0 ± 2.0 | 5.9 ± 0.4 |
| 5 | 7.3 ± 0.3 | — | 5.9 ± 0.1 |
| Reported value | 11.2 ± 2 | ** | ** |

*Serum samples were diluted 1:10,000 in VBS-gel and analyzed in duplicate. An IgG inhibition curve was included for a series of standard IgG samples from each species.
**Not available

DETERMINATION OF CELL BOUND IgG ANTI-FORSSMAN ANTIBODY $^{125}$I PA was used to measure IgG anti-Forssman antibody, isolated by chromatography of anti-Forssman antiserum on DEAE cellulose bound to the surface of either sheep erythrocytes (E) or tumor cells. Sensitized E were prepared by incubation at $10^9$/ml with an equal volume (0.1 ml) of IgG anti-Forssman antibody (A) at an appropriate concentration. The sensitized EA were washed with cold VBS-gel to remove unbound antibody and different numbers of cells were incubated with 0.1 ml (25,000 cpm) of $^{125}$I PA for differing times at 30° C. The cells were washed twice with VBS-gel and the amount of radiolabel associated with the cell pellets was determined. Control samples of unsensitized E and each dilution of antibody plus $^{125}$I PA were also carried through the experiment. The results show that approximately 70% of the radiolabel could be taken up by $10^7$ EA and that $5 \times 10^6$ EA (60% uptake) was an optimal cell concentration for measuring IgG binding.

DETECTION OF SOLUBLE TUMOR-ASSOCIATED ANTIGEN

An early report has demonstrated the presence of soluble tumor-associated antigen in the ascites fluid of guinea pigs inoculated with line-10 cells. Since the present invention has found that $^{125}$I PA can be used to measure tumor specific antibody on the surface of these cells, an experiment was conducted to determine if inhibition of binding could be used in the indirect detection of tumor-associated antigenic material present in the ascites fluid of tumor-bearing animals. Samples of pooled ascites fluid (free of cells) from six animals inoculated with either line-10 or line-1 cells were concentrated 10-fold and brought to approximately the same protein concentration with 0.15 M saline. Either buffer or dilutions of each sample (25 μl) were incubated with an equal volume of tumor-specific antiline-10 antiserum (1/20) for 1 hour at 37° C. These dilutions of antibody were used to sensitize $10^5$ line-10 cells (0.1 ml). After washing three times with cold VBS-gel, the cells were incubated with $^{125}$I PA (0.1 ml, 23,000 cpm) for 30 minutes at 30° C. After the cells were washed three times with buffer, the radioactivity associated with the cell pellets was counted. Control tubes included $^{125}$I PA plus cells, antibody alone or buffer alone. Significantly higher inhibition of antibody binding as measured by $^{125}$I PA uptake was observed with line-10 ascites compared to the line-1 fluid and the degree of inhibition was dependent on the amount of ascites fluid used. Compared to preincubation with buffer as control, no inhibition was observed when the highest concentration of either line-1 or line-10 ascites fluid were used to pretreat the line-10 cells before sensitization and incubation with $^{125}$I PA.

REAGENTS

Protein A was purchased from Pharmacia Fine Chemicals, Inc., Piscataway, N.J. Rabbit or goat IgG bound to agarose (approximately 3 μg IgG/mg beads), agarose beads functionalized with free carboxyl groups (Immunobeads), and Affi-gel 701 (polyacrylamide beads functionalized with free amino groups) were purchased from Bio-Rad Laboratories, Rockville, Centre, N.Y. Chromatographically pure IgG fractions, human IgM, and the IgG fractions of rabbit antisera to human chorionic gonadotropin (HCG), human IgM (heavy chain specific) and goat IgG (heavy and light chain) were purchased from Cappel Laboratories, Downington, Pa. Whole rabbit anti-methotrexate serum was supplied by Dr. Lawrence Levin, Department of Biochemistry, Bradeis University, Waltham, Mass.

Human chorionic gonadotropin (HCG) was purchased from Calbiochem, La Jolla, Calif., and methotrexate (MTX) was supplied by the Drug Evaluation Branch of the National Cancer Institute, NIH, Bethesda, Md. 1-Ethyl-3-(3-dimethylaminopropyl) carbodimide hydrochloride (EDAC) and compounds tested as inhibitors in the immunoassays were the highest quality reagents available and purchased from commercial sources.

EXAMPLE 1

Immunoassay for goat IgG

Goat IgG (a poor inhibitor) bound to agarose beads was tested for its ability to bind $^{125}$I PA. These results were compared to the binding observed when rabbit IgG beads were used. Under the test conditions, maximum binding (approximately 15,000 cpm) to the rabbit IgG beads was obtained when an amount of beads equivalent of 0.4 μg IgG was used. In contrast, the goat IgG beads failed to bind a significant amount of $^{125}$I PA even when an equivalent of 2.4 μg goat IgG was tested. Thus, the data in Table 2 below gave a quantitative measure of Protein A specificity for IgG from the 12 species tested.

Based on these observations a "sandwich" type radioimmunoassay for goat IgG was developed using the IgG fraction of rabbit antiserum to goat IgG and $^{125}I$ PA as the tracer. Optimal bead and rabbit antibody concentrations were determined as detailed for the HCG assay in Example 2. The ability of differing amounts of goat IgG and IgG from other species to inhibit the binding of rabbit anti-goat IgG to the beads was determined indirectly by measuring the inhibition of $^{125}I$ PA binding. Only 13 ng of goat IgG gave 50% inhibition of $^{125}I$ PA binding and 4.5 ng gave 15% inhibition. Sheep IgG also was an effective competitor since only 40 ng was required for 50% inhibition. In contrast, 10,000 ng of human, horse, rabbit or pig IgG gave no more than 20% inhibition. The general applicability of this method was demonstrated by developing assays for HCG, human IgM and methotrexate. In each case, $^{125}I$ PA was used as the radiolabelled tracer.

TABLE 2

Inhibition of Binding of $^{125}I$ Protein A to Immobilized Rabbit IgG by IgG From Different Species

| Species | Nanograms IgG Required to Inhibit by 50% |
| --- | --- |
| Rabbit | 60 |
| Human | 60 |
| Guinea pig | 60 |
| Pig | 135 |
| Dog | 290 |
| Cow | 3,000 |
| Mouse | 4,500 |
| Horse | 5,000 |
| Sheep | 40,000 |
| Goat | >100,000* |
| Rat | >100,000** |
| Chicken | >100,000** |

*45% inhibition at this level.
**>15% inhibition at this level.

EXAMPLE 2

Immunoassay for HCG

HCG bound to agarose beads was prepared. Different concentrations of the IgG fraction of rabbit anti-HCG binds differently to various amounts of the beads. With antibody diluted 1:250, a maximum binding of $^{125}I$ PA (approximately 25,500 cpm out of 37,000 cpm added) was achieved when 0.05 mg of beads was used. As more dilute antibody was used, the maximum number of cpm bound (as an indicator of bound HCG specific IgG) also decreased. Even when the antibody was diluted 1:6,750, over 3,500 cpm of added radioactivity was bound to the beads. In the absence of antibody, there was no significant binding of $^{125}I$ PA at any of the bead concentrations tested.

The binding of differing amounts of $^{125}I$ PA to 4 different concentrations of HCG beads that had been petreated with a 1:250 dilution of anti-HCG was determined. The highest amount of beads tested (0.08 mg) bound up to 50,000 cpm at the highest concentration (100,000 cpm) of $^{125}I$ PA. However, excess $^{125}I$ PA was not present under these conditions since the binding curve did not plateau. When 0.013 mg of beads was used, addition of approximately 35,000 cpm gave maximum binding (16,000 cpm), i.e., $^{125}I$ PA was in excess since addition of more radiolabel did not increase the binding significantly. With less beads, less $^{125}I$ PA was required to give maximum binding. Even when only 0.0014 mg of beads was used, a maximum of 2,000 cpm was bound compared to a background binding of 300 cpm to the beads in the absence of antibody. Based on these results, 38,000–40,000 cpm $^{125}I$ PA generally was added to 0.10–0.013 mg beads (50 μl) to give binding of approximately 15,000 cpm against a background of about 300 cpm. Under these conditions, or if fewer beads were used, $^{125}I$ PA was in excess.

EXAMPLE 3

Immunoassay for human IgM

The procedure described for the development of the HCG assay was used to establish optimal conditions for an assay for human IgM. The ability of differing amounts of human IgM and human IgG to inhibit the binding of the IgG fraction of rabbit anti-human IgM has been shown. Approximately 60 ng of IgM gave 50% inhibition and 15 ng gave 15% inhibition. In contrast, 16,000 ng of IgG was required to give 50% inhibition and approximately 3,500 ng failed to inhibit significantly. The possibility that the inhibition was due to IgM as a trace contaminant in the IgG preparation was not excluded. This assay was used to determine levels of IgM in the sera of 5 normal individuals. In addition, the corresponding levels of IgG were measured using an assay based on the inhibition of $^{125}I$ PA binding to rabbit IgG Immunobeads previously made. The IgM concentrations ranged from 0.57–1.74 mg/ml. The IgG levels ranged between 8.3–12.0 mg/ml and were consistent with reported normal levels.

EXAMPLE 4

Immunoassay for Methotrexate

In the above examples immunoassays were developed for antigenic macromolecules using the IgG fractions of antisera. To prepare the antigen-bead complexes, each antigen was bound covalently through free amino groups to carboxyl groups on the bead. To demonstrate more general application of this method, an assay was developed for the hapten methotrexate (MTX). MTX was coupled to keyhole limpet hemocyanin and injected into rabbits to produce anti-MTX antibodies. The whole serum was used in the assay along with MTX bound through its carboxyl groups to the free amino groups of Affi-gel 701 (polyacrylamide beads functionalized with free amino groups). The results show the binding of $^{125}I$ PA to differing amounts of MTX beads that were treated with whole antiserum at dilutions ranging between 1:250–1:6,750 or with buffer in the absence of antiserum. Under the conditions tested, up to 23,500 cpm were bound (antiserum 1:250 and 4.0 mg beads). Based on these results, an optimal set of conditions was established and the ability of folic acid and structurally related compounds to inhibit antibody binding was determined. The inhibition curves showed that approximately 800 pg of MTX gave 50% inhibition of binding and as little as 100 pg gave 15% inhibition. In contrast, greater than 10,000 ng of folic acid, 7,8-dihydrofolic acid (FAH$_2$), 5,6,7,8-tetrahydrofolic acid (FAH$_4$) and N-5-methyltetrahydrofolic acid were required for 50% inhibition. Even 10,000 ng of folinic acid (leucovorin), the drug used in "rescue" treatment of cancer patients after administration of high doses of MTX, failed to inhibit significantly. After MTX, aminopterin was the most effective competitor: 100 ng gave 50% inhibition. This was expected since aminoprotein resembles MTX more closely than the other folic acid analogs tested. The inhibition curve for MTX was the same if determined in the presence of human serum or urine. When concentrated serum (0.1 ml of 1:100 dilution) was analyzed by this method, significant binding of $^{125}$I PA to the tube occurred presumably due to IgG binding non-specifically to the glass. When this occurred, the beads were transferred to new tubes before they were counted.

I claim:

1. A method of making $^{125}$I-labelled Protein A (PA) for use utilizing as a tracer for the quantitative determination of proteins and haptens in physiological fluids comprising the preparation of $^{125}$I PA from $^{125}$I which has been evaporated from benzene and attached to Protein A in an amino acid mixture, followed by gel separation.

2. $^{125}$I-labelled Protein A which has been prepared by the process of claim 1.

3. A method of use of the product of claim 2 wherein $^{125}$I PA is used with purified rabbit IgG bound to a solid support to develop a competitive binding assay or measurement of a substance selected from the group consisting of Protein A, human, rabbit and guinea pig IgG at the nanogram level.

4. A method of use of the product of claim 2 or 3 wherein the competitive binding assay detects human IgG at the nanogram level.

5. A method of use of the product of claim 2 wherein the $^{125}$I PA is utilized to detect IgG anti-Forssman antibody bound to sheep erythrocytes.

6. A method of use of the product of claim 2 wherein the $^{125}$I PA is utilized to detect line-1 and line-10 tumor cells as an indirect assay for tumor associated antigen.

7. A method of use of the product of claim 2 wherein the $^{125}$I PA is utilized to detect methotrexate.

8. A method of use of the product of claim 3 wherein the $^{125}$I PA is utilized to detect leucovorin.

* * * * *